United States Patent
Xu et al.

(10) Patent No.: US 9,759,630 B2
(45) Date of Patent: Sep. 12, 2017

(54) SYSTEM FOR DETECTING COOLANT LEAKS IN GENERATORS

(71) Applicant: General Electric Company, Schenectady, NY (US)

(72) Inventors: James Jun Xu, Niskayuna, NY (US); James Jonathan Grant, Niskayuna, NY (US); James Wilson Clark, Schenectady, NY (US); Marlowe Cameron Bjorklund, Daphne, AL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/263,455

(22) Filed: Sep. 13, 2016

(65) Prior Publication Data
US 2016/0377502 A1    Dec. 29, 2016

Related U.S. Application Data

(63) Continuation-in-part of application No. 14/249,581, filed on Apr. 10, 2014, now Pat. No. 9,488,629.

(51) Int. Cl.
| | | |
|---|---|---|
| *G01M 3/20* | (2006.01) | |
| *G01N 33/00* | (2006.01) | |
| *G01N 21/3504* | (2014.01) | |
| *G01M 3/22* | (2006.01) | |
| *G01M 3/38* | (2006.01) | |
| *G01M 3/00* | (2006.01) | |
| *G01N 25/72* | (2006.01) | |

(52) U.S. Cl.
CPC .............. *G01M 3/20* (2013.01); *G01M 3/002* (2013.01); *G01M 3/228* (2013.01); *G01M 3/38* (2013.01); *G01N 21/3504* (2013.01); *G01N 33/004* (2013.01); *G01N 25/72* (2013.01)

(58) Field of Classification Search
CPC ..... G01M 3/20; G01N 21/3504; G01N 33/004
USPC ........................................................ 73/40.7
See application file for complete search history.

(56) References Cited

U.S. PATENT DOCUMENTS 7,134,322 B1 *  11/2006  Baird ................. G01M 3/22
                                                     73/40.5 R
2006/0091310 A1 *  5/2006  Furry ................. G01J 5/061
                                                     250/330

FOREIGN PATENT DOCUMENTS

ES    WO 2010049569 A1 *  5/2010  ............ G01M 3/226

OTHER PUBLICATIONS

English translation of Gallego et al., WO 2010/049569, May 6, 2010, 27 pages.*

* cited by examiner

*Primary Examiner* — Hezron E Williams
*Assistant Examiner* — David Z Huang
(74) *Attorney, Agent, or Firm* — James W. Pemrick; Ernest G. Cusick; Frank A. Landgraff (57) ABSTRACT

A system for detecting a gas leak in a generator includes a source of carbon dioxide gas, and a subsystem for introducing the carbon dioxide gas into the generator. An infrared imaging device is adapted to communicate with a notification device to display an image of at least a portion of the generator and the carbon dioxide gas. The infrared imaging device is a cooled detector and a filter with a spectral response between about 3 μm and about 5 μm. At least one of the detector and the filter is cooled to between about −80° C. and about −200° C. The gas leak will be indicated on the notification device.

19 Claims, 9 Drawing Sheets

SYSTEM FOR DETECTING COOLANT LEAKS IN GENERATORS

CROSS-REFERENCE TO RELATED APPLICATIONS

This application is a continuation-in-part of application Ser. No. 14/249,581, filed on Apr. 10, 2014, hereby incorporated by reference.

BACKGROUND OF THE INVENTION

The subject matter disclosed herein generally relates to detection of leaks and more particularly to the online detection of coolant leaks in hydrogen cooled generators.

Large generators are typically cooled with a light density gas. Hydrogen ($H_2$) has been widely used as a coolant due to its desirable thermophysical properties including low windage friction, high heat dissipation capability and high resistance to corona discharge when compared to other cooling gas options. Additionally, $H_2$ has the advantage of being readily accessible and inexpensive.

Leakage of $H_2$ may prevent the generator from operating efficiently, and in some cases may create power generation outages. Among possible areas of $H_2$ leakage around a generator, are flanged joints on the stator casing including high voltage bushings, seal casings and pipe flanges. Leaks may also occur around the interfaces of the cooler, welds, bolt heads and end shield. The bearing enclosure in the outer end shields, the rotor terminal packing, collector assembly as well as glands made for instrumentation wiring penetration may also be susceptible to leaks. Other air-tight transitions and welding joints may be sources of leaks, as well as the seal oil drain system, gas piping, and hydrogen cabinet. If the generator is a water cooled generator the stator liquid cooled windings also may be a source of leaks.

$H_2$ leaks are difficult to detect because $H_2$ is colorless, odorless, symmetric in a molecular structure, and because of its low density it dissipates quickly when it leaks into the atmosphere. The technical challenges in monitoring and detecting a potential $H_2$ leak lie in identifying the exact location of $H_2$ leaking in a turbine generator, especially in inaccessible and space limited areas. Typically, a hydrogen leak is indicated when the generator begins consuming more hydrogen than usual. In this scenario the operators are aware that a leak exists, but the location of the leak is unknown.

Conventional turbine generator leak detection methods require the purging of the off-grid or off-line turbine generator with air and thereafter bringing it up to normal operating pressure. Then a long check list of areas to be examined and a step-by-step method of elimination are used. Each cycle of the testing requires monitoring for at least 24 hours. If the leakage is higher than recommended a variety of methods of leak detection have been used.

For example, a bubble test may be performed using soapy water or a similar detergent solution applied over all the accessible areas of possible leaks. Another approach is to use a halogen leak detector designed for detecting leaks in a pressurized system where halogen compound gases (such as Freon 12) are used as a tracer gas to check for leaks. The exterior of the system is then scanned with a sniffer probe sensitive to traces of the halogen-bearing gas. The principle is based on the increased positive ions (K or Na) emission because of sudden halide composition presence.

All conventional methods of leak detection require the detector to be in close proximity to the source of the leak and take considerable time to implement. Most of the conventional methods use close or near contact "sniffer" technology and probes. These methods are painstakingly time consuming and in some cases miss the gas leaks if they occurred from an internal seal crack. If the inaccessible $H_2$ sealing system or constrained space is the source of a possible leak, considerable effort to disassemble the turbine generator may be needed, commonly resulting in delaying the schedule several more days. Values approaching $1 MM loss of operating revenue per day have been reported by power producers when a turbine generator is forced to be off-line.

Long wave gas detection cameras (detector response of 10-11 µm) have been used in the electrical distribution industry to detect leakage of Sulfur Hexafluoride ($SF_6$) from high voltage switchgear and transformers. It has also been proposed to use $SF_6$ as a tracer gas in finding $H_2$ leaks in power plant generators in combination with backscatter/absorption technology. The backscatter/absorption leak detection process uses an active scanning laser to provide a directed energy source to irradiate a target area. The laser beam is reflected back to the source camera tuned to a specific frequency band. $SF_6$ has high affinity to absorb this frequency of energy and appear as a dark cloud on the camera monitor. The camera monitor provides a direct indication of how serious the leaks are by the size and darkness of the tracer gas cloud.

However, the major issues associated with the use of $SF_6$ as a tracer gas relate to environmental, health, and safety concerns and the potential deterioration of generator insulation systems and retaining rings. $SF_6$ is a potent and hazardous gas with an atmospheric lifetime of 3,200 years. Release of $SF_6$ to the environment after detection, or the remaining residue at ppm (parts per million) level is of environmental, health, and safety concern to personnel in the detecting areas. Additionally, in the presence of potential corona activities and thermal stress during turbine generator operations, $SF_6$ can decompose into harmful by-products. These byproducts include HF, $SF_4$, $SO_2$, and $SO_2F_2$ which are toxic gases. In the presence of moisture, the primary and secondary decomposition products of $SF_6$ form corrosive electrolytes which may cause damage and operational failure to an $H_2$ cooled generator. For example, $SF_6$ and its degradation byproduct have known corrosion effects on generator field retaining ring material whose main composition is 18Cr-18C stainless steel.

Existing methods do not provide a remote, sensitive, accurate, safe, fast, non-corrosive or on-line detection capability.

BRIEF DESCRIPTION OF THE INVENTION

The disclosure provides a method and system for the remote, sensitive, accurate, safe, fast and on-line detection of an $H_2$ leak from an $H_2$ cooled generator that avoids health, environmental and safety concerns as well as avoiding corrosion of generator components. The method and system provide for manual or automatic introduction of a tracer gas so that tracer gas injection may be performed regularly in a controlled manner with the least disturbance imposed to gas pressure of an on-grid generator. The method and system also provide introducing tracer gas without derating an on-grid generator, and/or the introduction of a tracer gas into a gas medium other than $H_2$ such as nitrogen or argon inside of a generator which may be in state of idling, or turning-gear, but may be brought online quickly.

In accordance with one aspect of the invention, a system for detecting a gas leak in a generator includes a source of carbon dioxide gas, and a subsystem for introducing the carbon dioxide gas into the generator. An infrared imaging device is adapted to communicate with a notification device to display an image of at least a portion of the generator and the carbon dioxide gas. The infrared imaging device is a cooled detector and a filter with a spectral response between about 3 μm and about 5 μm. At least one of the detector and the filter is cooled to between about −80° C. and about −200° C. The gas leak is indicated on the notification device.

In another aspect, a system for detecting a gas leak in a dynamoelectric machine is provided. The dynamoelectric machine is on-line, on-grid or on turning gears. The system includes a source of a non-corrosive tracer gas, and a subsystem for introducing the non-corrosive tracer gas into the machine. An infrared imaging device is adapted to communicate with a notification device to display an image of at least a portion of the machine and the non-corrosive tracer gas. The infrared imaging device has a cooled detector and a filter with a spectral response between about 3 μm and about 5 μm. At least one of the detector and the filter is cooled to between about −80° C. and about −200° C. The gas leak will be indicated on the notification device.

In yet another aspect, a system for detecting a gas leak in a hydrogen cooled generator that is on-line or on-grid is provided. The system includes a source of a non-corrosive tracer gas, where the non-corrosive tracer gas is carbon dioxide ($CO_2$). A subsystem is used for introducing the non-corrosive tracer gas into the hydrogen cooled generator. An infrared imaging device is adapted to communicate with a notification device to display an image of at least a portion of the generator and the non-corrosive tracer gas. The infrared imaging device comprises a cooled detector and a filter with a spectral response between about 4.2 μm and about 4.5 μm. At least one of the detector and the filter is cooled to between about −80° C. and about −200° C. The gas leak will be indicated on the notification device.

BRIEF DESCRIPTION OF THE DRAWINGS

Other features and advantages of the present invention will be apparent from the following more detailed description of the preferred embodiment, taken in conjunction with the accompanying drawings which illustrate, by way of example, the principles of certain aspects of the invention.

DETAILED DESCRIPTION OF THE INVENTION

Aspects of the present disclosure include a system for detecting a gas leak in a generator through the introduction of an environmentally safe and non-corrosive tracer gas into an on-grid generator. An infrared imaging device adapted to display an image of the escaping tracer gas is provided.

Figure 1:
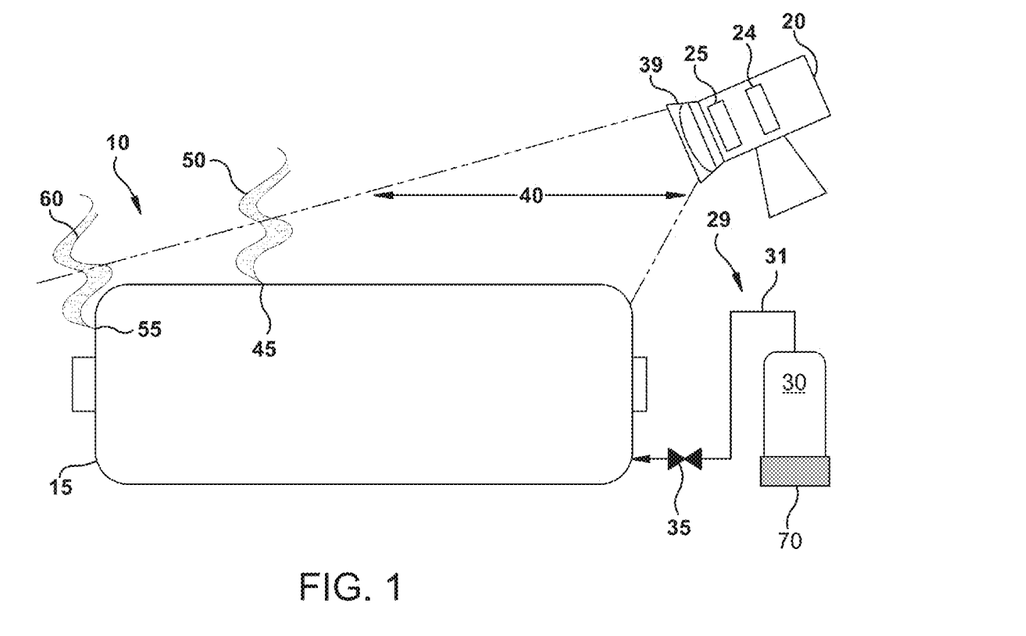
FIG. 1 illustrates a schematic view of a leak detection system, according to an aspect of the present invention.

FIG. 1 illustrates a schematic of a system 10 for detecting a gas leak for use with a hydrogen ($H_2$) cooled generator 15. Generator 15 is a dynamoelectric machine and the present invention may be applied to any generator or motor, including but not limited to, a pressurized generator, a pressurized gas cooled generator, a pressurized air cooled generator or a pressurized cooled motor. The leak detection system 10 includes an infrared imaging device 20 capable of scanning large or small portions of the $H_2$ cooled generator 15. The infrared imaging device may include lenses made with germanium or other infrared transparent glass materials. The infrared imaging device 20 may be a portable, hand held, midwave infrared camera with a detector 24 having a response of about 3 μm to about 5 μm and may be further spectrally adapted to about 4.2 μm to about 4.5 μm by use of a filter 25. In addition, infrared imaging device 20 may be a handheld imaging device, a video camera, a smartphone, or a tablet. The filter 25 restricts the wavelengths of radiation allowed to pass through to the detector 24 to a very narrow band called the band pass. This technique is called spectral adaptation. This makes the infrared imaging device 20 most responsive to gases that can be used as tracer gases. In other aspects of the invention, one or more filters 25 may be used in series, for example, a first filter with a spectral response of 3 μm to 5 μm may be stacked in series with a second filter having a spectral response of 4.2 μm to 4.5 μm.

The leak detection system 10 may include a subsystem 29 for introducing a tracer gas, including a source of tracer gas 30 coupled to the $H_2$ cooled turbine generator 15 through conduit 31 and control valve 35. An automatic tracer gas injection system (not shown) may include an algorithm and be monitored in a turbine deck control room if the automatic tracer gas injection is employed for large volume turbogenerators. The infrared imaging device 20 may include an outer lens 39 that provides the infrared imaging device 20 with a field of view 40 encompassing a portion of the $H_2$ cooled turbine generator 15. For example, the lens 39 may have a fixed focal length of about 14 mm to about 60 mm, or more. The lens 39 may also comprise a multi-focal lens having a range of focal lengths (e.g., a zoom lens). In general, most uses will be inside buildings, so a wider field of view (lower numerical focal length such as 25 mm or 12.5 mm) may be preferred. However, a narrow field of view (higher numerical focal length such as 50 mm or 100 mm) may be advantageous to pinpoint the exact leaking location(s) in some applications. If there is a leak point 45 on the $H_2$ cooled generator 15 the leaking gas will generate a leak gas cloud 50 emanating from the leak point 45. Similarly, if there is a leak point 55 on the $H_2$ cooled turbine generator 15 the leaking gas will generate a leak gas cloud 60 emanating from the leak point 55. Leak gas cloud 50 and leak gas cloud 60 will contain tracer gas capable of being detected by the infrared imaging device 20.

In operation, the infrared imaging device 20 displays an image of the leaking gas cloud 50 by rendering opaque (or visible) the tracer gas in the leak gas cloud 50. For many gases, the ability to absorb infrared radiation depends on the wavelength of the radiation and temperature difference between leaking tracer gases and ambient. In other words, their degree of transparency varies with wavelength, and detecting sensitivity with temperature differential. There may be infrared wavelengths where they are essentially opaque due to absorption. The infrared imaging device 20 is adapted to visualize the absorptive and emissive properties of tracer gases allowing the user the ability to discern the tracer gas from its host environment. The filter 25 is designed to transmit in an infrared spectrum that is coincident in wavelength with vibrational/rotational energy transitions and emission of the molecular bonds of the tracer gas. These transitions and emissions are typically strongly coupled to the field via dipole moment changes in the molecule, and are common to many types of gases and vapors. The detector 24 and/or filter 25 of the infrared imaging device 20 may be cooled to about −80° C. to about −200° C. in an Integrated Cooler Detector Assembly (IDCA), to increase the sensitivity of remote imaging of tracer gases. In some applications, the filter may be cooled to temperatures higher (i.e., warmer) than −80° C., but lower than room (i.e., ambient) temperature. For example, the filter may be exposed to ambient temperature on one side of the filter whereas the opposing side of the filter is exposed to a −80° C. or −200° C. environment. The thermal sensitivity is typically less than 20 mK, and more preferably less than 14 mK. The filter 25 may be mounted on the outer lens 39, or behind the outer lens 39, or inside the IDCA assembly for increased sensitivity. The device may be calibrated and tuned with the largest contrast possible using modes of absorption, reflection or scattering or emission so that the exact pressure, flow rate and temperature gradient of leaking tracer gas may be identified from varying detection distances.

If the infrared imaging device 20 is directed at an $H_2$ cooled generator 15 without a gas leak, objects in the field of view will emit and reflect infrared radiation through the filter 25 of the infrared imaging device 20. The filter 25 will allow only certain wavelengths of radiation through to the detector 24 and from this the infrared imaging device 20 will generate an uncompensated image of gaseous radiation intensity. If there is a leak within the field of view 40 of the infrared imaging device 20 such as at leak point 45, a leaking gas cloud (or plume) 50 will be generated at the leaking locale and may dissipate between the $H_2$ cooled turbine generator 15 and the infrared imaging device 20. The gas cloud 50 will contain tracer gas that absorbs and emits radiation in the band pass range of the filter 25, and consequently the amount of background radiation passing through the cloud and returning to the detector 24 will be reduced, thereby making the tracer gas cloud visible through the infrared imaging device 20. If there is a leak outside of the field of view 40 of the infrared imaging device 20 such as at leak point 55, the portions of the leak gas cloud 60 would still be detected by the infrared imaging device 20. If desired, the corresponding level of $H_2$ can be estimated.

The tracer gas and its decomposition products, if any, should be environmentally safe from the point of view of toxicity. The tracer gas is preferably non-corrosive. Additionally, the tracer gas should not cause damage to generator insulation systems, or corrosive damage to steel retaining rings, and fan blades. Tracer gases may include hydrocarbon gases such as, for example Butane, Ethane, Heptane, Propane and the like. Preferably the tracer gas may be carbon dioxide ($CO_2$), which has unlimited mixing limits with both air and hydrogen. In addition, $CO_2$ is typically already present on site, as it is one of such intermediate gases used in the normal start-up and shut-down purging procedures in utility scale generators. The background absorption of the $CO_2$ content of the atmosphere (400 ppm) may be eliminated when $CO_2$ is used as the tracer gas at concentrations greater than 400 ppm. The subsystem 29 may also include a weight measuring scale 70 that is configured to monitor the weight of carbon dioxide used, so that introduction of carbon dioxide may be ceased when a predetermined weight has been reached. For example, for specific dynamoelectric machines the amount (i.e., weight) of carbon dioxide needed may be known, and in this case once the weight (e.g., 1 pound) has been introduced then the valve 35 can be closed. The weight example given is merely one example, and it is to be understood that any appropriate weight may be chosen according to the specific generator under test.

Figure 2:
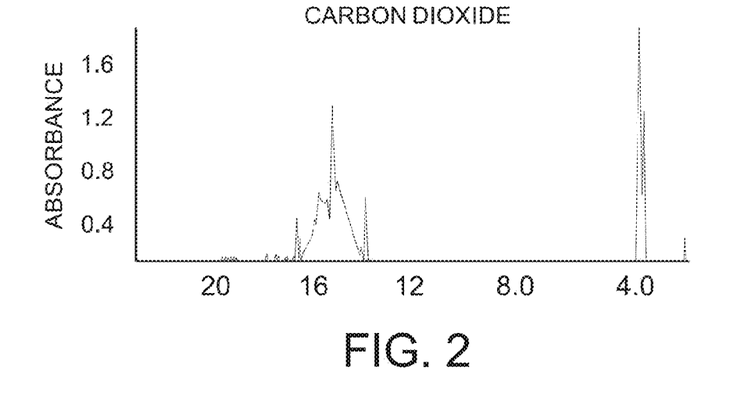
FIG. 2 is a chart of the absorption spectrum of $CO_2$.
Figure 3:
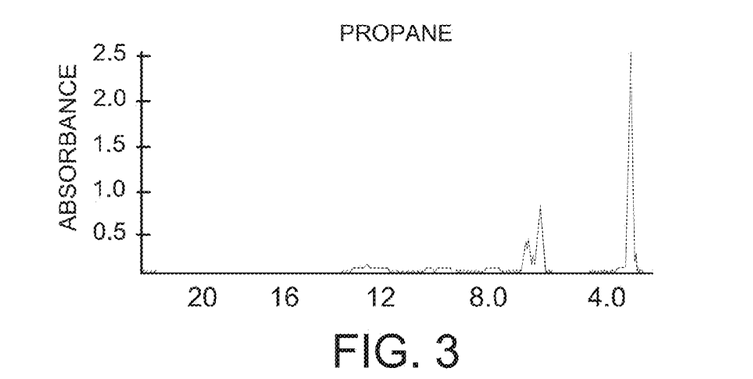
FIG. 3 is a chart of the absorption spectrum of Propane.
Figure 4:
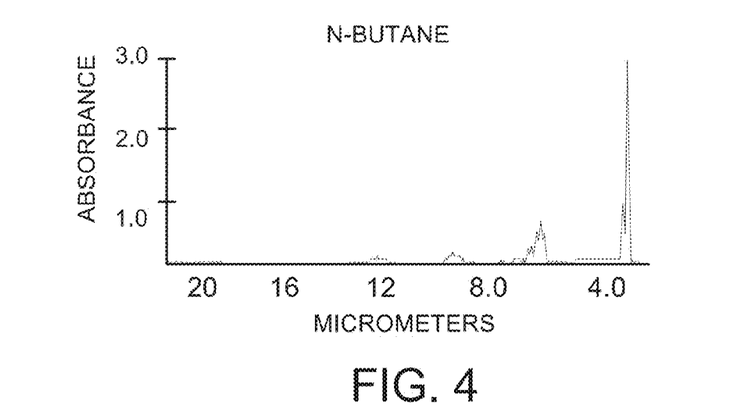
FIG. 4 is a chart of the absorption spectrum of n-Butane.
Figure 5:
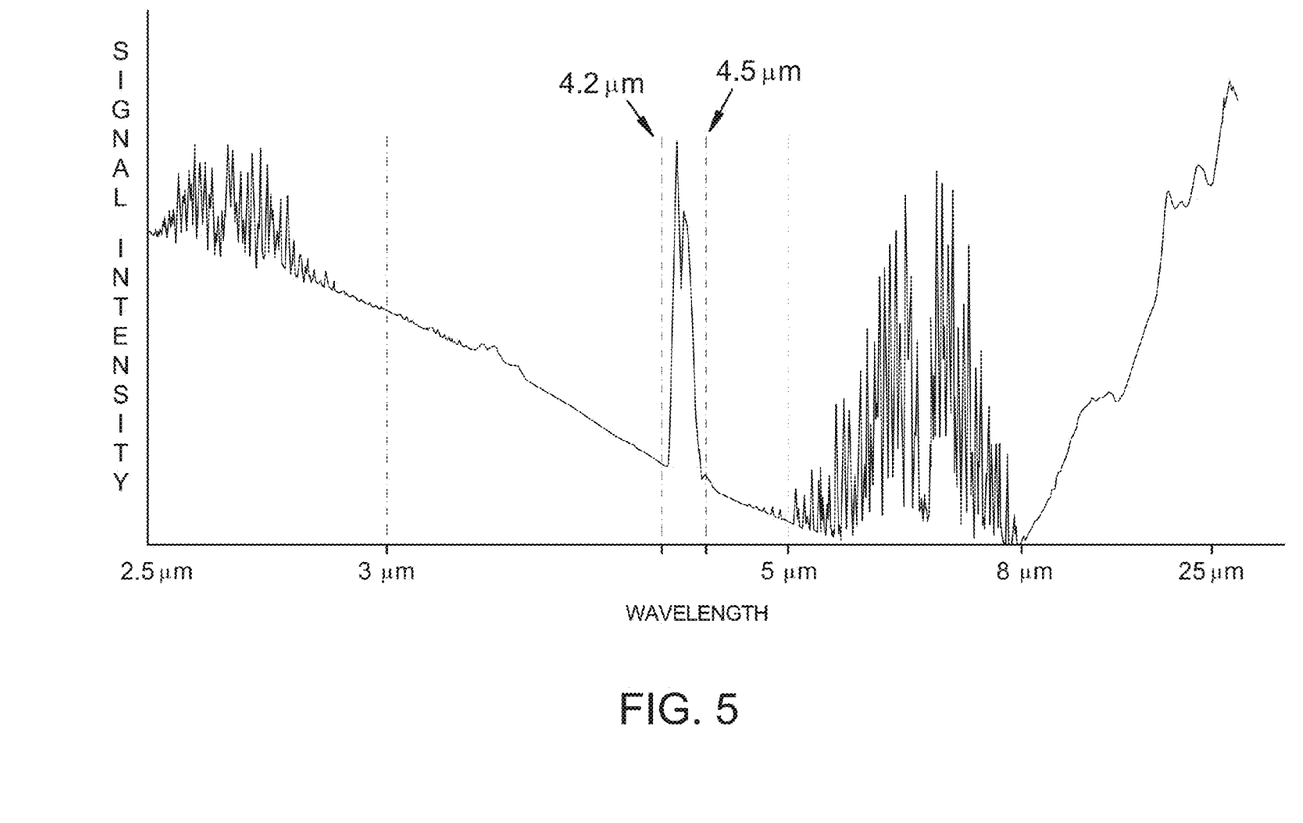
FIG. 5 illustrates the infrared signal intensity of various gases over various wavelengths.

Illustrated in FIGS. 2, 3 and 4 are the absorption spectra of $CO_2$, propane and n-butane respectively. As can be seen from the charts, $CO_2$, propane and n-Butane have a maximal absorption peak of $CO_2$ near 4.3 μm that can be detected by a midwave infrared imaging device 20. FIG. 5 illustrates the infrared signal intensity of various gases over various wavelengths. In the wavelength range of 2.5 μm to less than 3 and 5 μm to 8 μm, water ($H_2O$) molecules have a strong infrared signal. The infrared signal intensity of hydrocarbons is fairly linear over the wavelength range of 3 μm to 5 μm, more specifically, in the range of 3.33 μm to 3.57 μm, except for a peak at about 4.2 μm to about 4.5 μm. This peak at 4.2 μm to 4.5 μm is due to carbon dioxide ($CO_2$). This means that $CO_2$ will be easy to distinguish (visually) from background radiation in this relatively narrow infrared band, assuming the detector and filter are tuned to this wavelength band. The difficulty arises in that most detectors can't detect or distinguish infrared signals in this band, due to overwhelming background interference. However, according to an aspect of the present invention, a cooled infrared detector or imaging device having a filter of about 3 μm to about 5 μm, or more specifically, about 4.2 μm to about 4.5 μm, will be capable of detecting carbon dioxide. The cooled detector aspect reduces photon interference that typically plagues other detectors, and the band pass filter eliminates interference from other commonly present gases or molecules by focusing on the high contrast (or intensity) signal of carbon dioxide.

Figure 6:
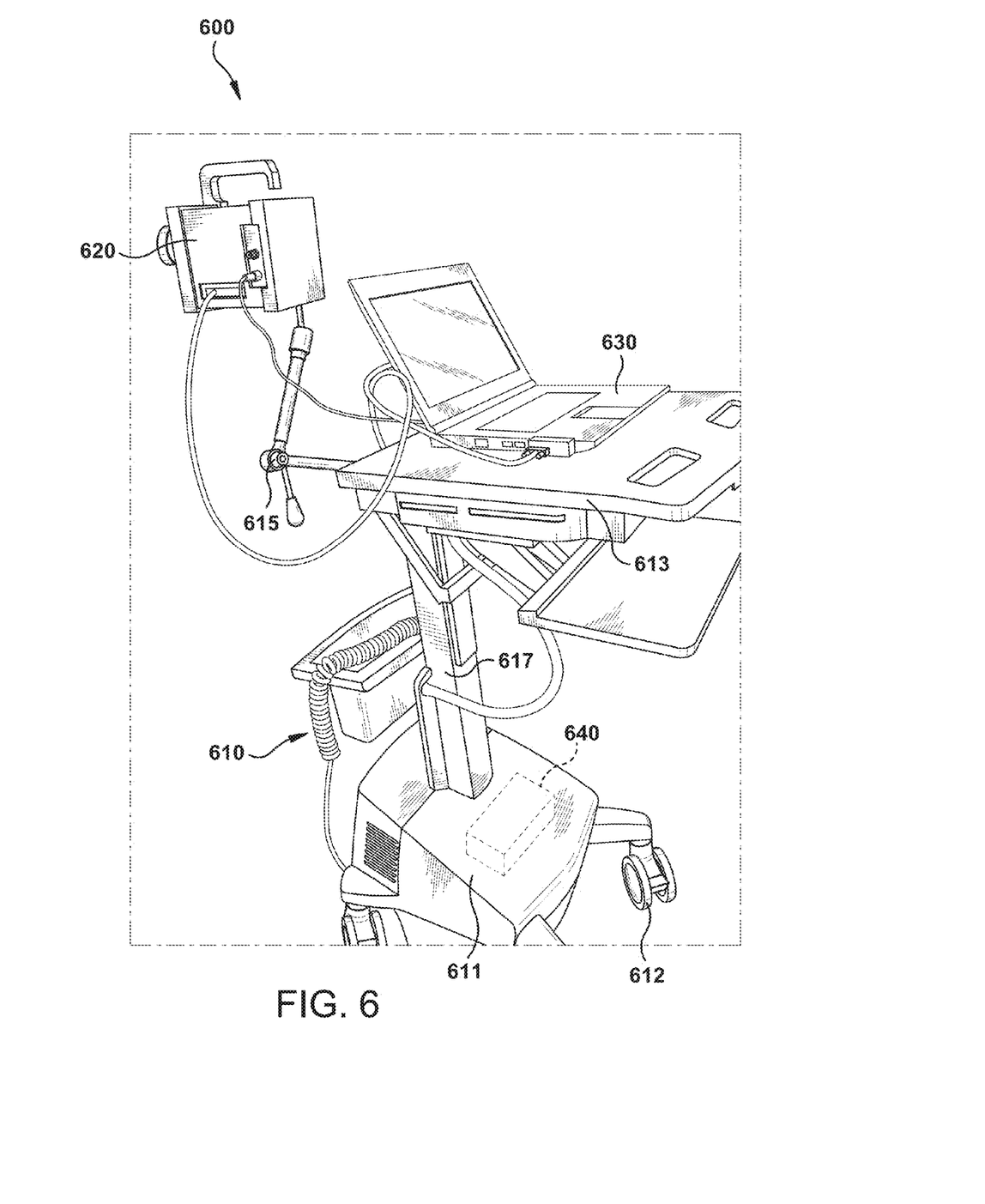
FIG. 6 illustrates a partial perspective view of the system for detecting a gas leak in a hydrogen cooled generator, according to an aspect of the present invention.

FIG. 6 illustrates a partial perspective view of the system 600 for detecting a gas leak in a hydrogen cooled generator. The system 600 includes a movable cart 610 that is configured to facilitate movement of the infrared imaging device 620 and a notification device (or display) 630 around the hydrogen cooled generator 15. The cart 610 includes a base 611 having a plurality of wheels 612. The wheels 612 may be swivel caster wheels having a single, double, or compound wheel configuration. The wheels 612 are attached to the base 611 so as to enable the cart 610 to be easily moved. The wheels 612 may be comprised of rubber, plastic, nylon, aluminum, or stainless steel, or combinations thereof. A hinged arm 615 is connected to the cart and the infrared imaging device may be attached to the arm 615. The arm 615 allows the infrared imaging device to be moved into a variety of positions and facilitates aiming of the infrared imaging device 620. A support arm 617 allows the working platform 613 to be adjusted for height and position. The platform 613 may function as a support for the infrared imaging device 620 and display 630.

The infrared imaging device 620 was described previously, and is a cooled infrared imaging detector, such as an IDCA camera, and may be mounted to platform 613 or the extendable and/or flexible arm 615. The imaging device 620 may also be removed from the platform 613 or arm 615 and moved independently around the generator by an operator or technician. The imaging device 620 may be connected to the notification device 630 by a wired or wireless link. A wired link may be a USB connection, serial or parallel connectors/cables, video cable or any other suitable wired connection. A wireless link may include a bluetooth, wifi, radio frequency, or any other suitable wireless communication system/interface. The notification device 630 may take the form of a special or general purpose digital computer, such as a personal computer (PC; IBM-compatible, Apple-compatible, Android or otherwise), laptop, netbook, tablet, smartphone, workstation, minicomputer, or any other suitable computer and display device. The notification device 630 receives image data from the imaging device 620 and displays the result in real time, or near real time, on a display. The platform 616 may include a battery or battery bank 640 which may be certified to be used on a generator turbine deck (i.e., a class 1, division 2 hazardous location) environment to provide power to the notification device 630 and camera 620. The battery bank 640 may be housed on the base 611 or it may be incorporated into the platform 613 so that it resides under notification device 630. In this manner, the system 600 is a self-contained and powered mobile system that can be easily moved around the generator 15 and positioned to image specific regions of interest. As an alternative, the infrared imaging device may also be a handheld imaging device, a video camera, a smartphone, or a tablet.

The notification device 630 may also display a warning or notification that a potential leak has been detected. An optional text message 730 (illustrated in FIG. 7) or display can be shown on the notification device 630. For example, text 730 could flash on and off, or be displayed in a high-contrast color. The high-contrast color could be white on a grayscale display, or red on a color display, or any other suitable high contrast color that facilitates identification. An audible signal (e.g., a beep or siren) can be output from a speaker associated with the notification device 630. A border 740 could be drawn around the potential leak cloud 720 on the display of the notification device. A fax could be sent to a fax machine indicating the leak has been detected. A text message (or image or video or alarm) could be sent to a smartphone, tablet or computer indicating leak detection. A signal could also be sent to a remote or local monitoring site to indicate that a leak was detected.

Figure 7:
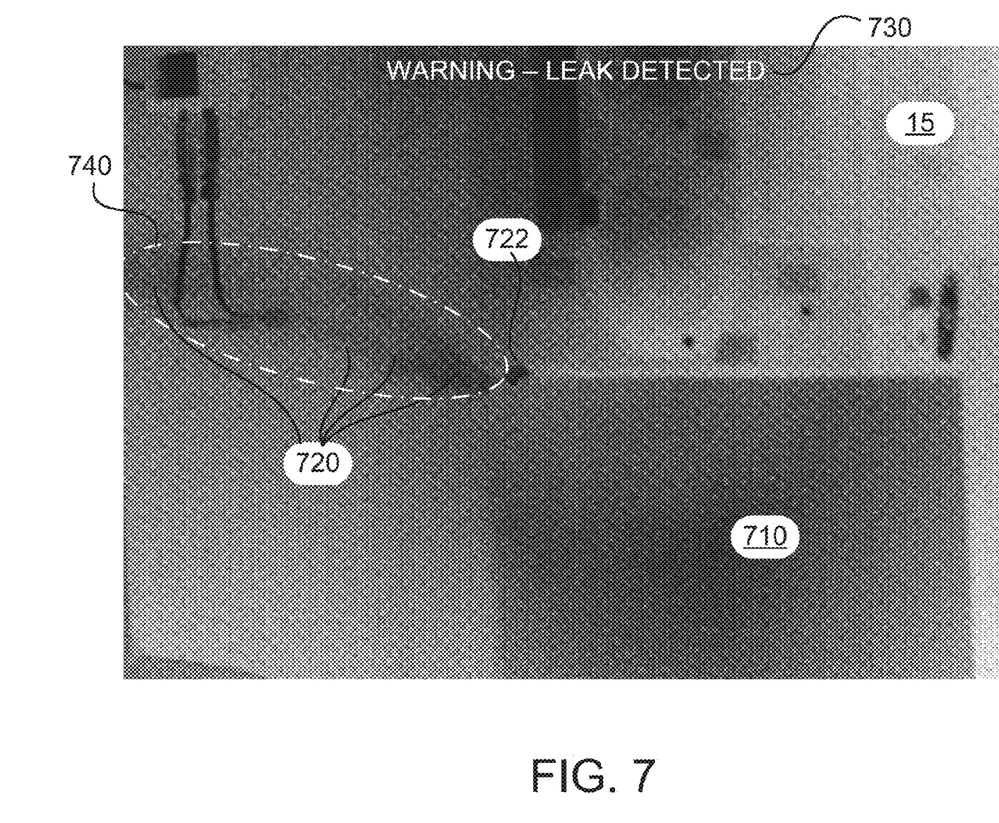
FIG. 7 illustrates a screenshot capture from the infrared imaging device and display during leak detection, according to an aspect of the present invention.

FIG. 7 illustrates a screenshot capture from the infrared imaging device 620 and display of notification device 630 during a leak detection. A portion of the generator 15 is shown and the top of the hydrogen cabinet door 710 is in the field of view of camera 620. A leaking dark cloud 720 can be seen emanating from a corner of the door 710. The leak begins at point 722 and the gas cloud 720 is blowing or drifting to the left (as shown). In this example, the $H_2$ cooled generator 15 is in operation and/or generating power (or on-line). The $CO_2$ tracer gas (which is non-corrosive) is escaping from a leak somewhere in the hydrogen cabinet. The gas cloud 722 is invisible to the naked eye, but is made visible on the display or notification device 630 via a midwave infrared imaging device 620 and the appropriate filters (e.g., a 3 μm to 5 μm, or more specifically, 4.2 μm to 4.5 μm bandpass optical filter). In the example of FIG. 7, a 3 μm to 5 μm bandpass optical filter was used. FIG. 7 shows a static photograph (or screen capture), but even in a still image it will be clear that something is concerning in the image, as the dark gas cloud 720 should not be there in a non-leaking generator 15. The camera 620 and display 630 can be used to display video images as well, and with a video display the gas cloud 720 can be seen to physically move on the display of notification device 630. The relative motion between the moving gas cloud 720 and the static (or non-moving generator parts) makes it very easy for a person to identify that a leak is occurring and where the leak begins. In this example, the hydrogen cabinet door can be opened and another scan can take place to pinpoint the exact leak location.

Figure 8:
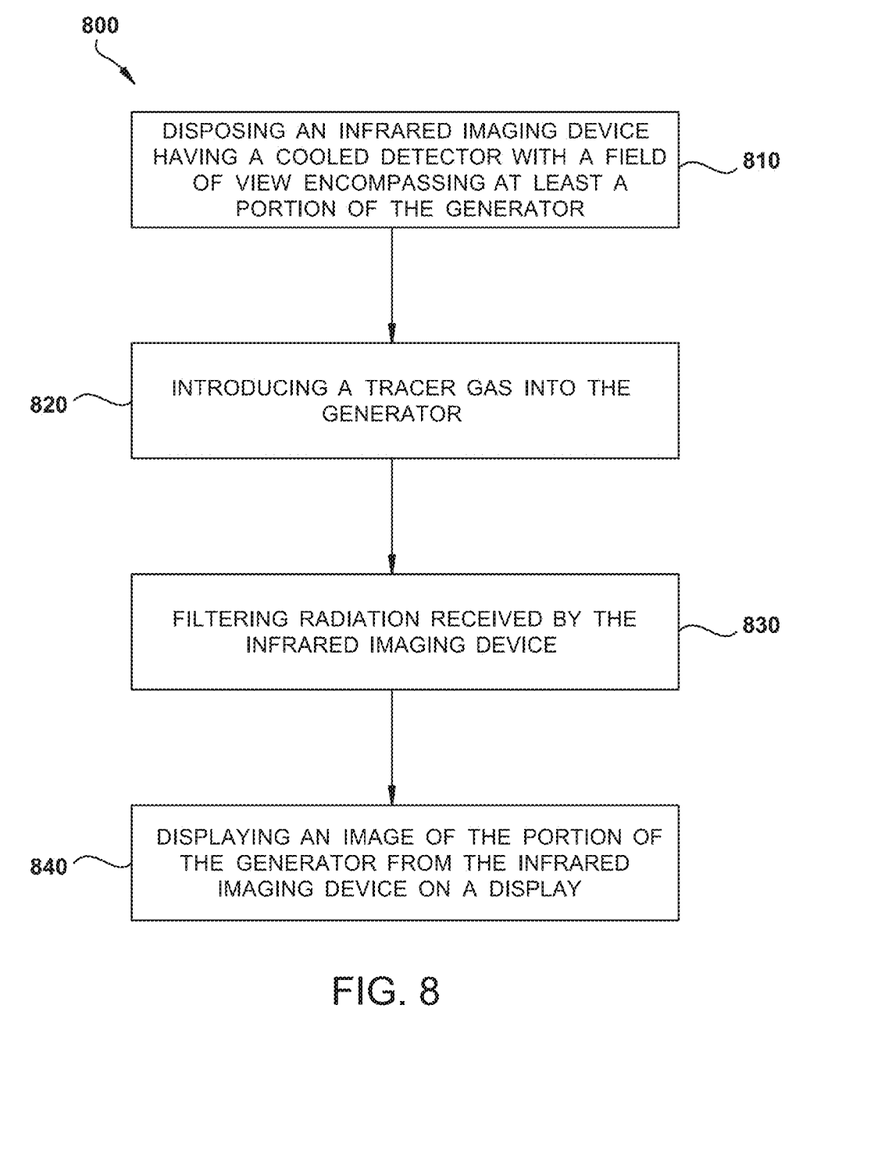
FIG. 8 illustrates is a flow chart of a method for detecting a gas leak in a hydrogen cooled generator, according to an aspect of the present invention.

FIG. 8 illustrates a flow chart of a method 800 for detecting a gas leak in a hydrogen cooled generator 15, according to an aspect of the present invention. The method 800 includes the steps of disposing 810 an infrared imaging device 620 having a cooled detector with a filter having a spectral response between about 3 μm to about 5 μm with a field of view encompassing at least a portion of the generator 15. The disposing step 810 may also include using a movable cart 610 that contains one or both of the infrared imaging device 620 or the notification device 630 to position the infrared imaging device 620 or the notification device 630 around the generator 15.

An introducing step 820 introduces a tracer gas into the generator 15. The generator is on-line and the tracer gas has an absorption spectrum of between about 3 μm and about 5 μm. The introducing step 820 may also include removing some of the hydrogen to lower pressure in the generator by about 2 PSI to about 10 PSI, and/or injecting carbon dioxide into the generator until the pressure in the generator rises by about 2 PSI to about 10 PSI. The introducing step may include injecting carbon dioxide into the generator until the hydrogen purity inside the generator is about 90% to about 95%, or injecting carbon dioxide into the generator, monitoring the weight of carbon dioxide used, and ceasing injection of carbon dioxide when a predetermined weight of $CO_2$ has been reached. The subsystem 29 may be configured to remove some of the hydrogen to lower pressure in the generator by about 2 PSI to about 10 PSI, and to inject carbon dioxide into the generator until the pressure in the generator rises by about 2 PSI to about 10 PSI.

A filtering step 830 filters radiation received by the infrared imaging device 620 in the absorption spectrum of the tracer gas. The filtering step 830 may include filtering the radiation with a filter having a spectral response between about 4.2 μm and about 4.5 μm. The method 800 may also include cooling the detector and/or the filter to between about −80° C. and about −200° C., to increase sensitivity to the tracer gas and reduce interference from other atmospheric constituents.

A display step 840 displays an image of the portion of the generator 15 from the infrared imaging device 620 on a display of notification device 630. The gas leak will be indicated by a cloud 720 of tracer gas leaking from the generator 15 on the display. The display step 840 may also include displaying a moving cloud on the display if a leak is detected. A video signal may be used to display a video image that is displayed in real time or near real time.

Figure 9:
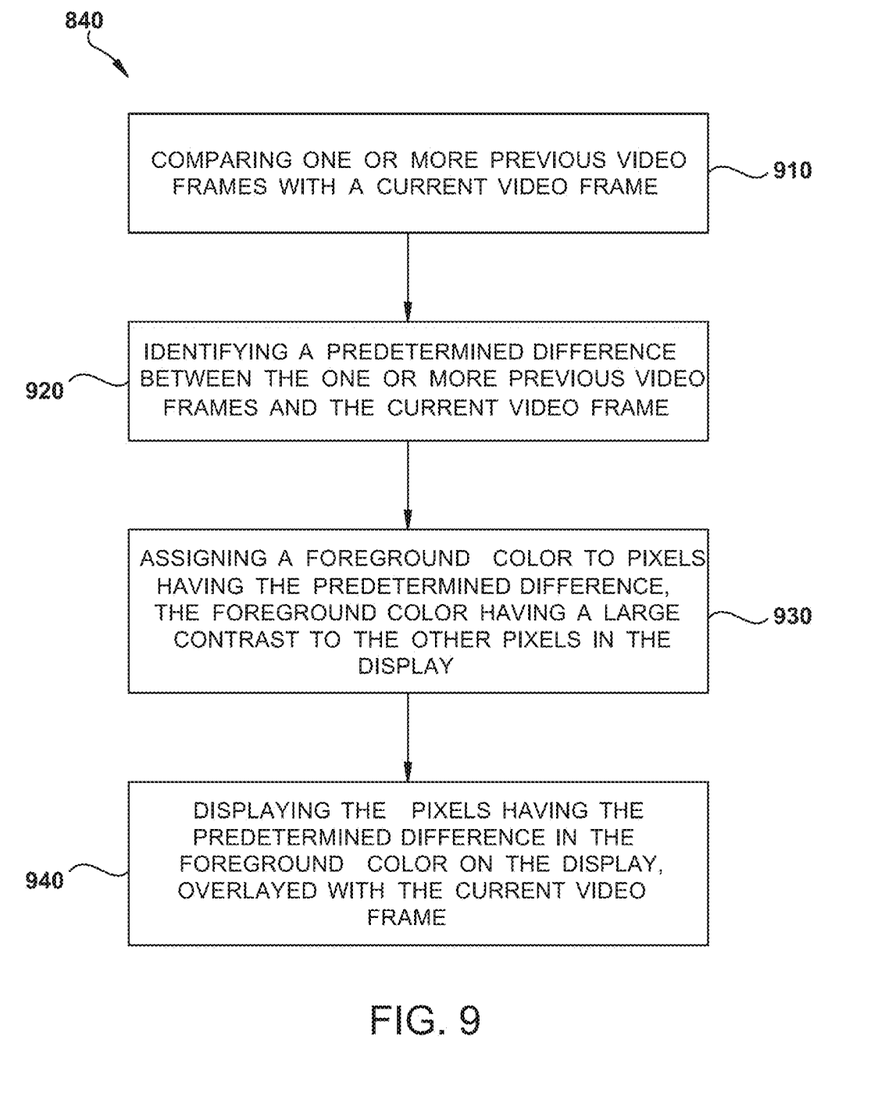
FIG. 9 illustrates is a flow chart of the displaying step, according to an aspect of the present invention.

FIG. 8 illustrates a flowchart of optional steps for use with the display step 840 of FIG. 7. The display step 840 may further include a comparing step 910 that compares one or more previous video frames with a current video frame. An identifying step 920 identifies a predetermined difference between the one or more previous video frames and the current video frame. An assigning step 930 assigns a foreground color to pixels having the predetermined difference, and the foreground color has a large contrast to the other pixels in the display. For example, if the primary color scheme of the image is grayscale (or black and white), then the foreground color may be red, which would provide a large contrast and make the moving red pixels easily visible against a grayscale background. A display step 940 is used to display the pixels having the predetermined difference in the foreground color on the display, overlaid with the current video frame. In this manner, it will be easy for a user (or technician) to identify if a leak is occurring, and where the leak is occurring.

Alternatively, the display step 840 may include a comparing step that compares one or more previous video frames with a current video frame, and an identifying step that identifies a predetermined difference between the one or more previous video frames and the current video frame. An assigning step assigns a foreground color to a border surrounding the pixels having the predetermined difference, and the foreground color has a large contrast to the other pixels in the display. A displaying step displays the border, around the pixels having the predetermined difference, in the foreground color on the display, where the border overlaid with the current video frame. For example, if the primary color scheme of the image is grayscale (or black and white), then the border color may be red, green or yellow, which would provide a large contrast and make the moving red, green or yellow pixels easily visible against a grayscale background. Any color may be chosen to provide contrast, as desired in the specific application or by the needs of the specific user. For example, a color blind person may choose a specific color that has a large contrast from their perception.

The display step 840 may also include a comparing step that compares one or more video frames with an adjacent video frame, and an identifying step that identifies a predetermined difference between the one or more video frames and the adjacent video frame. An assigning step assigns at least one of, a foreground color to pixels having the predetermined difference or a foreground color to a border surrounding the pixels having the predetermined difference. The foreground color has a large contrast to other pixels in the display. A displaying step displays at least one of, the pixels having the predetermined difference in the foreground color on the display, or the border in the foreground color on the display around the pixels having the predetermined difference, overlaid with a current video frame.

The notification device 630 and frame comparator system 1000 of the invention can be implemented in software (e.g., firmware), hardware, or a combination thereof. In the currently contemplated best mode, the frame comparator system 1000 is implemented in software, as an executable program, and is executed by a special or general purpose digital computer, such as a personal computer (PC; IBM-compatible, Apple-compatible, or otherwise), laptop, tablet, smartphone, workstation, minicomputer, or mainframe computer. An example of a general purpose computer that can implement the frame comparator system 1000 of the present invention is shown in FIG. 10.

Figure 10:
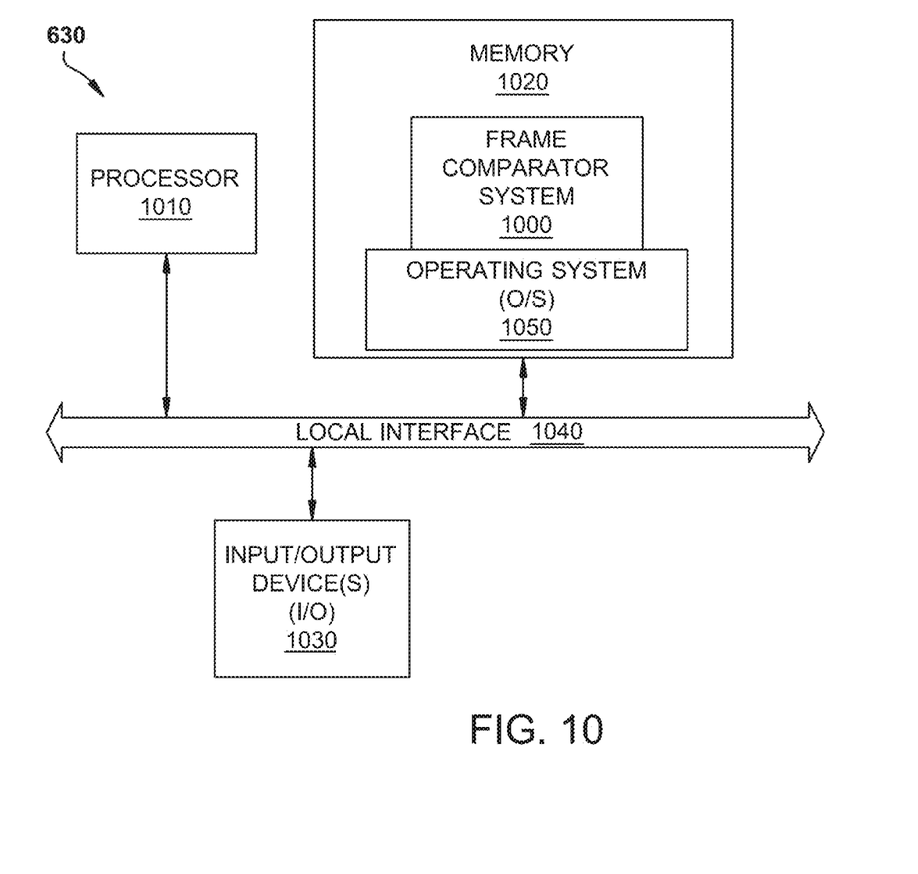
FIG. 10 illustrates is a schematic of the display used for displaying an image used during leak detection, according to an aspect of the present invention.

Generally, in terms of hardware architecture, as shown in FIG. 10, the computer or display 630 includes a processor 1010, memory 1020, and one or more input and/or output (I/O) devices 1030 (or peripherals) that are communicatively coupled via a local interface 1040. The local interface 1040 can be, for example but not limited to, one or more buses or other wired or wireless connections, as is known in the art. The local interface 1040 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1010 is a hardware device for executing software, particularly that stored in memory 1020. The processor 1010 can be any custom made or commercially available processor, a central processing unit (CPU), an auxiliary processor among several processors associated with the computer 630, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, a core 2 or i7 series microprocessor from Intel Corporation, a PowerPC microprocessor from IBM, a Sparc microprocessor from Sun Microsystems, Inc, or a 68xxx series microprocessor from Motorola Corporation.

The memory 1020 can include any one or combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory 1020 may incorporate electronic, magnetic, optical, and/or other types of storage media. Note that the memory 1020 can have a distributed architecture, where various components are situated remote from one another, but can be accessed by the processor 1010.

The software in memory 1020 may include one or more separate programs, each of which comprises an ordered listing of executable instructions for implementing logical functions. In the example of FIG. 1, the software in the memory 1020 includes the frame comparator system 1000 in accordance with the present invention and a suitable operating system (O/S) 1050. A nonexhaustive list of examples of suitable commercially available operating systems 1050 is as follows: (a) a Windows operating system available from Microsoft Corporation; (b) a Netware operating system available from Novell, Inc.; (c) a Macintosh operating system available from Apple Computer, Inc.; (e) a UNIX operating system, which is available for purchase from many vendors, such as the Hewlett-Packard Company, Sun Microsystems, Inc., and AT&T Corporation; (d) a LINUX operating system, which is freeware that is readily available on the Internet; (e) a run time Vxworks operating system from WindRiver Systems, Inc.; or (f) an appliance-based operating system, such as that implemented in handheld computers or personal data assistants (PDAs) (e.g., PalmOS available from Palm Computing, Inc., and Windows CE available from Microsoft Corporation). The operating system 1050 essentially controls the execution of other computer programs, such as the frame comparator system 1000, and provides scheduling, input-output control, file and data management, memory management, and communication control and related services. In addition, a graphics processing unit (not shown) resident on a motherboard (not shown) may also be used to implement the frame comparator system 1000.

The frame comparator system 1000 is a source program, executable program (object code), script, or any other entity comprising a set of instructions to be performed. When a source program, then the program needs to be translated via a compiler, assembler, interpreter, or the like, which may or may not be included within the memory 1020, so as to operate properly in connection with the O/S 1050. Furthermore, the frame comparator system 1000 can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada.

The I/O devices 1030 may include input devices, for example but not limited to, a keyboard, mouse, scanner, microphone, camera, infrared imaging device or camera, etc. Furthermore, the I/O devices 1030 may also include output devices, for example but not limited to, a printer, display, etc. Finally, the I/O devices 1030 may further include devices that communicate both inputs and outputs, for instance but not limited to, a modulator/demodulator (modem; for accessing another device, system, or network), a radio frequency (RF), wifi, Bluetooth or other transceiver, a telephonic interface, a bridge, a router, etc.

If the computer 630 is a PC, workstation, or the like, the software in the memory 1020 may further include a basic input output system (BIOS) (omitted for simplicity). The BIOS is a set of essential software routines that initialize and test hardware at startup, start the O/S 1050, and support the transfer of data among the hardware devices. The BIOS is stored in ROM so that the BIOS can be executed when the computer 630 is activated.

When the computer 630 is in operation, the processor 1010 is configured to execute software stored within the memory 1020, to communicate data to and from the memory 1020, and to generally control operations of the computer 630 pursuant to the software. The frame comparator system 1000 and the O/S 1050, in whole or in part, but typically the latter, are read by the processor 1010, perhaps buffered within the processor 1010, and then executed.

When the frame comparator system 1000 is implemented in software, as is shown in FIG. 10, it should be noted that the frame comparator system 1000 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The frame comparator system 1000 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the frame comparator system 1000 is implemented in hardware, the frame comparator system 1000 can implemented with any or a combination of the following technologies, which are each well known in the art: a graphics processing unit, a video card, a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc. The infrared imaging device may be adapted to compare one or more previous video frames with a current video frame, identify a predetermined difference between the one or more previous video frames and the current video frame, assign a foreground color to pixels having the predetermined difference, the foreground color contrasting to the other pixels in a display of the notification device, and to display the pixels having the predetermined difference in the foreground color on the display, overlaid with the current video frame.

Figure 11:
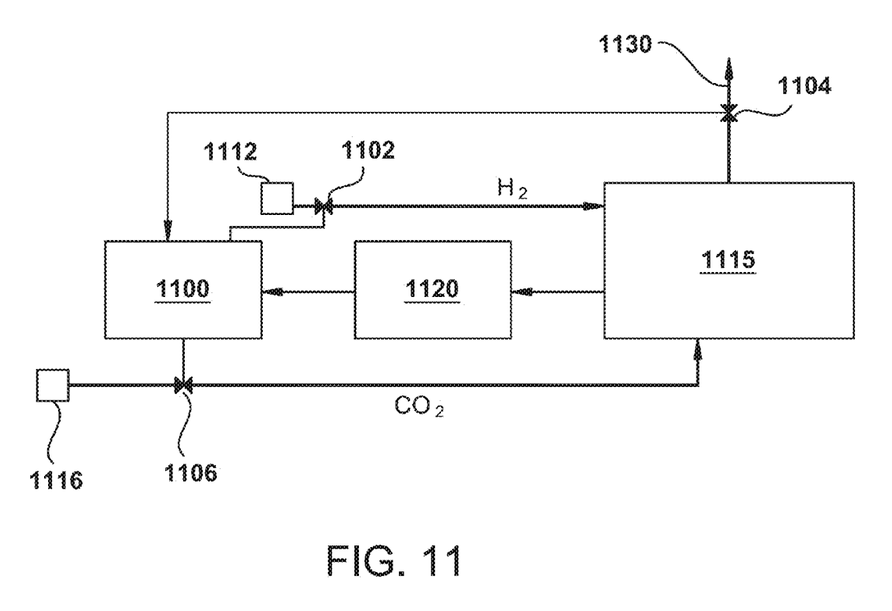
FIG. 11 illustrates a schematic of an automatic tracer gas injection system mounted on an existing $CO_2$ purging pipeline in a gas manifold of a generator, which may be below the turbine deck.

FIG. 11 illustrates a schematic of an automatic tracer gas injection control system 1100. The control system 1100 may be mounted in the manifold area associated with generator 1115, and may be monitored in a control room. The algorithm used by the automatic injection control system 1100 monitors both $H_2$ purity and gas pressure in the generator 1115. The $H_2$ feeding valve 1102 is first turned off, and hydrogen supplied from $H_2$ supply 1112 is ceased. $H_2$ vent flow through scavenging pipe 1130 is controlled to be on and off to match the introduction of the tracer gas, via $H_2$ vent valve 1104. The $CO_2$ injection valve 1106 controls $CO_2$ supply from a $CO_2$ source 1116. The $CO_2$ injection valve 1106 may be adjusted based on the gradual reduction of $H_2$ purity, by monitoring $H_2$ purity meter 1120. The pressure in the generator 1115 may fluctuate slightly (e.g., fluctuation within 3%, and preferably within 2%, and more preferably within <1%). The introduction of tracer gas is controlled between 1% to 10% in volume so that total $H_2$ purity in the casing may be always above 90%. Knowing that $CO_2$ may act as a non-air gas medium, 90% $H_2$ purity in this tertiary gas mixture in the generator 1115 may actually be "inaccurate" as the real $H_2$ purity may be close to its original $H_2$ purity prior to the introduction of $CO_2$. The automatic control of tracer gas introduction may be preferable for large generators so that the introduction can be accomplished in about 30 minutes to about 90 minutes.

Manual introduction of a tracer gas may be practiced when the generator is relatively small (e.g., <100 MW) with a casing volume below 1000 cubic feet and gas volume below 3,000 cubic feet. This may be achieved by either lowering about 5% casing pressure prior to the introduction, or weighing consumption of the tracer gas bottle on a scale after calculating the needed volume of a tracer gas. The injecting step may include controlling an injection flow of the non-corrosive tracer gas based upon feedback of a gas pressure, an $H_2$ purity, and flow through the $H_2$ scavenging pipe 1130. The automatic tracer gas control system 1100 targets gradual reduction of the $H_2$ purity while keeping the gas pressure inside of the generator 1115 substantially stable, and the gas pressure swing is within about 5% of a gas pressure original value. The step of introducing the tracer gas may also include injecting carbon dioxide into the generator 1115, where the generator has a cooling gas media of argon or nitrogen while the generator is on turning gears or on-line.

A turning gear may be engaged when there is no steam (for a steam turbine) or no combustion gas flow (for a gas turbine) to slowly rotate the turbine to ensure even heating to prevent uneven expansion. The generator is typically mechanically connected to the output of the gas or steam turbine. After first rotating the turbine by the turning gear, allowing time for the rotor to assume a straight plane (no bowing), then the turning gear may be disengaged and steam is admitted to the turbine or gas combustion flow begins in the gas turbine. The terms "on turning gears", "on-line" or "on-grid" may be viewed as equivalent from the generator perspective, because the generator will be in some state of operation.

The $H_2$ purity meter 1120 is typically calibrated based upon the thermal conductivity of a binary gas medium of air and hydrogen. The introduction of a tracer gas may result in the purity meter reading slightly higher than the actual $H_2$ purity in the generator casing. For a 5% volume of $CO_2$ injection into an on-grid generator with starting $H_2$ purity in the casing at 98%, the actual $H_2$ purity may be at 92.8% in the casing if the $H_2$ purity meter reads 93%, or the actual $H_2$ purity may be at 93% in the casing if the $H_2$ purity meter reads at 93.2%.

The simulated temperature increase in stator windings, stator cores and rotor may be well within specified design limits for almost all generators up to about 600 MW output with the introduction of about 5% volume of $CO_2$. The windage loss may be increased, but fan pressure differential increase may be too small to make any deflection on the fan tip typically made with steel alloy materials. Total KW loss may be increased by less than 5% at 5% volume of $CO_2$ introduction from the level prior to $CO_2$ introduction. Therefore, de-rating of the on-grid (or on-line) generator in rated days and hot days may not be required.

The tracer gas such as $CO_2$ may also be introduced into a non hydrogen gas media such as nitrogen and or argon when either of them present in a generator either on-line or on-grid or on turning gears. A $CO_2$ purity meter may be used for this application. An example using a hydrogen cooled generator was described, however, any suitable machine may be used with the system and method of the present invention. The machine may be a generator, a pressurized generator, a hydrogen cooled generator, an air cooled generator, a turbine, a steam turbine, a gas turbine, a motor or a compressor.

The system and method according to the present invention demonstrates substantially improved results that were unexpected because a leak can now be detected in an on-line, on-grid or on turning gears generator. Previously, the generator had to be taken off-line and a time consuming and expensive process was needed for leak detection, and/or the hydrogen leak was effectively invisible to the naked eye. The substantially improved results are obtained by scanning an on-line or operating generator and by using an infrared imaging device configured to detect a leaking gas cloud emanating from the generator.

Where the definition of terms departs from the commonly used meaning of the term, applicant intends to utilize the definitions provided below, unless specifically indicated. The terminology used herein is for the purpose of describing particular embodiments only and is not intended to be limiting of the invention. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Where the definition of terms departs from the commonly used meaning of the term, applicant intends to utilize the definitions provided herein, unless specifically indicated. The singular forms "a", "an" and "the" are intended to include the plural forms as well, unless the context clearly indicates otherwise. It will be understood that, although the terms first, second, etc. may be used to describe various elements, these elements should not be limited by these terms. These terms are only used to distinguish one element from another. The term "and/or" includes any, and all, combinations of one or more of the associated listed items. The phrases "coupled to" and "coupled with" contemplates direct or indirect coupling.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. The terms "about" and "approximately" as applied to a particular value of a range applies to both values, and unless otherwise dependent on the precision of the instrument measuring the value, may indicate +/−10% or +/−20% of the stated value(s).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements.

The invention claimed is:

1. A system for detecting a gas leak in a generator, the system comprising:
 a source of carbon dioxide gas;
 a subsystem for introducing the carbon dioxide gas into the generator;
 an infrared imaging device adapted to communicate with a notification device to display an image of at least a portion of the generator and the carbon dioxide gas, the infrared imaging device comprising a cooled detector and a filter with a spectral response between 3 μm and 5 μm, wherein at least one of the detector and the filter is cooled to between −80° C. and −200° C., wherein the infrared imaging device is adapted to compare one or more previous video frames with a current video frame, identify a predetermined difference between the one or more previous video frames and the current video frame, assign a foreground color to pixels having the predetermined difference, the foreground color contrasting to the other pixels in a display of the notification device, and to display the pixels having the predetermined difference in the foreground color on the display, overlaid with the current video frame; and wherein the gas leak will be indicated on the notification device.

2. The system of claim 1, wherein the generator is a hydrogen cooled generator that is on-line or on-grid.

3. The system of claim 2, wherein the spectral response of the filter is between 4.2 µm and 4.5 µm.

4. The system of claim 3, wherein both the detector and filter are cooled.

5. The system of claim 4, further comprising:
a movable cart that is configured to facilitate movement of the infrared imaging device and the notification device around the generator, or
the infrared imaging device is one of a handheld imaging device, a video camera, a smartphone, or a tablet.

6. The system of claim 3, wherein the subsystem is configured to remove some of the hydrogen to lower pressure in the generator by 2 PSI to 10 PSI, and to inject carbon dioxide into the generator until the pressure in the generator rises by 2 PSI to 10 PSI.

7. The system of claim 3, the subsystem including a weight measuring scale configured to monitor the weight of carbon dioxide used, so that introduction of carbon dioxide is ceased when a predetermined weight has been reached.

8. A system for detecting a gas leak in a dynamoelectric machine, the dynamoelectric machine is on-line, on-grid or on turning gears, the system comprising:
a source of a non-corrosive tracer gas;
a subsystem for introducing the non-corrosive tracer gas into the machine;
an infrared imaging device adapted to communicate with a notification device to display an image of at least a portion of the machine and the non-corrosive tracer gas, the infrared imaging device comprising a cooled detector and a filter with a spectral response between 3 µm and 5 µm, wherein at least one of the detector and the filter is cooled to between −80° C. and −200° C., wherein the infrared imaging device is adapted to compare one or more previous video frames with a current video frame, identify a predetermined difference between the one or more previous video frames and the current video frame, assign a foreground color to pixels having the predetermined difference, the foreground color contrasting to the other pixels in a display of the notification device, and to display the pixels having the predetermined difference in the foreground color on the display, overlaid with the current video frame; and
wherein the gas leak will be indicated on the notification device.

9. The system of claim 8, wherein the non-corrosive tracer gas is carbon dioxide ($CO_2$).

10. The system of claim 9, wherein the spectral response of the filter is between 4.2 µm and 4.5 µm.

11. The system of claim 10, wherein both the detector and the filter are cooled.

12. The system of claim 9, further comprising:
a movable cart that is configured to facilitate movement of the infrared imaging device and the notification device around the generator, or
the infrared imaging device is one of a handheld imaging device, a video camera, a smartphone, or a tablet.

13. The system of claim 9, wherein the subsystem is configured to remove some of the hydrogen to lower pressure in the generator by 2 PSI to 10 PSI, and to inject carbon dioxide into the generator until the pressure in the generator rises by 2 PSI to 10 PSI.

14. The system of claim 9, the subsystem including a weight measuring scale configured to monitor the weight of carbon dioxide used, so that introduction of carbon dioxide is ceased when a predetermined weight has been reached.

15. A system for detecting a gas leak in a hydrogen cooled generator that is on-line or on-grid, the system comprising:
a source of a non-corrosive tracer gas, the non-corrosive tracer gas is carbon dioxide ($CO_2$);
a subsystem for introducing the non-corrosive tracer gas into the hydrogen cooled generator;
an infrared imaging device adapted to communicate with a notification device to display an image of at least a portion of the generator and the non-corrosive tracer gas, the infrared imaging device comprising a cooled detector and a filter with a spectral response between 4.2 µm and 4.5 µm, wherein at least one of the detector and the filter is cooled to between −80° C. and −200° C., wherein the infrared imaging device is adapted to compare one or more previous video frames with a current video frame, identify a predetermined difference between the one or more previous video frames and the current video frame, assign a foreground color to pixels having the predetermined difference, the foreground color contrasting to the other pixels in a display of the notification device, and to display the pixels having the predetermined difference in the foreground color on the display, overlaid with the current video frame; and
wherein the gas leak will be indicated on the notification device.

16. The system of claim 15 wherein both the detector and filter are cooled.

17. The system of claim 15, further comprising:
a movable cart that is configured to facilitate movement of the infrared imaging device and the notification device around the generator, or
the infrared imaging device is one of a handheld imaging device, a video camera, a smartphone, or a tablet.

18. The system of claim 17, wherein the subsystem is configured to remove some of the hydrogen to lower pressure in the generator by 2 PSI to 10 PSI, and to inject carbon dioxide into the generator until the pressure in the generator rises by 2 PSI to 10 PSI.

19. The system of claim 18, the subsystem including a weight measuring scale configured to monitor the weight of carbon dioxide used, so that introduction of carbon dioxide is ceased when a predetermined weight has been reached.

* * * * *